(12) United States Patent
Hillairet et al.

(10) Patent No.: US 7,786,232 B2
(45) Date of Patent: Aug. 31, 2010

(54) SINGLE SITE CATALYST SYSTEMS HAVING A SCORPION-LIKE STRUCTURE

(75) Inventors: Caroline Hillairet, Soignies (BE); Guillaume Michaud, Lille (FR); Sirol Sabine, Horrues (BE)

(73) Assignee: Total Petrochemicals Research Feluy, Seneffe(Feluy) (BE)

( * ) Notice: Subject to any disclaimer, the term of this patent is extended or adjusted under 35 U.S.C. 154(b) by 0 days.

(21) Appl. No.: 11/994,976

(22) PCT Filed: Jul. 6, 2006

(86) PCT No.: PCT/EP2006/063994

§ 371 (c)(1),
(2), (4) Date: Nov. 6, 2008

(87) PCT Pub. No.: WO2007/006740

PCT Pub. Date: Jan. 18, 2007

(65) Prior Publication Data

US 2009/0264609 A1  Oct. 22, 2009

(30) Foreign Application Priority Data

Jul. 7, 2005  (EP) .................................. 05106166

(51) Int. Cl.
*C08F 4/06* (2006.01)
(52) U.S. Cl. ...................................... 526/172; 502/162
(58) Field of Classification Search ................. 526/172; 502/162

See application file for complete search history.

(56) References Cited

U.S. PATENT DOCUMENTS

2003/0224927 A1 * 12/2003 Shih ........................... 502/103

FOREIGN PATENT DOCUMENTS

| EP | 1046647 A | 10/2000 |
| WO | WO 01/34665 A | 5/2001 |

* cited by examiner

*Primary Examiner*—Ling-Siu Choi
*Assistant Examiner*—Sonya Wright
(74) *Attorney, Agent, or Firm*—Tenley R. Krueger (57) ABSTRACT

The present invention discloses single site catalyst systems having a scorpion-like three dimensional structure that are suitable for oligomerising or polymerising ethylene and alpha-olefins.

17 Claims, 2 Drawing Sheets

FIG. 1

Molecular weight distribution curve of example 5

FIG. 2

Molecular weight distribution curves of examples 10, 12, 14 and 15

SINGLE SITE CATALYST SYSTEMS HAVING A SCORPION-LIKE STRUCTURE

The present invention related to the field of single site catalyst systems having scorpion-like three dimensional structure that are suitable for oligomerising or polymerising ethylene and alpha-olefins.

There exists a multitude of catalyst systems available for polymerising or oligomerising ethylene and alpha-olefins, but there is a growing need for finding new systems capable to tailor polymers with very specific properties. More and more post-metallocene catalyst components based on early or late transition metals from Groups 3 to 10 of the Periodic Table have recently been investigated such as for example those disclosed in Gibson and al. review (Gibson, V. C.; Spitzmesser, S. K., Chem. Rev. 2003, 103, p. 283). But there is still a need to improve either the specificities or the performances of these systems.

It is an aim of the present invention to provide a new single site catalyst components based on beta-diimine ligands with a chelating pendant arm.

It is also an aim of the present invention to provide single site catalyst components having a scorpion-like spatial organisation.

It is another aim of the present invention to provide active catalyst systems based on these catalyst components.

It is a further aim of the present invention to provide a process for polymerising or for oligomerising ethylene and alpha-olefins with these new catalyst systems.

It is also an aim of the present invention to provide a polyethylene by polymerising ethylene with these new catalyst systems.

Accordingly, the present invention discloses a ligand of formula I

I wherein R1, R2, R3, R4, R5, R6, R7, R8, R9 and R10 are each independently selected from hydrogen, unsubstituted or substituted hydrocarbyl, or inert functional group. Two or more of those the groups can themselves be linked together to form further ring or rings.

R1 and R3, R2 and R4, and R9 and R10, cannot be simultaneously oxazoline wherein Z is selected from groups 15 or 16 of the Periodic Table and m is the valence of Z minus one.

By inert functional group, is meant a group, other than hydrocarbyl or substituted hydrocarbyl, that is inert under the complexation conditions to which the compound containing said group is subjected. They can be selected for example from halo, ester, ether, amino, imino, nitro, cyano, carboxyl, phosphate, phosphonite, phosphine, phosphinite, thioether and amide. Preferably, they are selected from halo, such as chloro, bromo, fluoro and iodo, or ether of formula —OR* wherein R* is unsubstituted or substituted hydrocarbyl. After metallation of the ligand, an inert functional group must not coordinate to the metal more strongly than the groups organised to coordinate to the metal and thereby displace the desired coordinating group.

It results from the reaction between a beta-diimine II and a compound of formula III wherein X is a leaving group, preferably halogen for example Br.

Preferably, R1 and R2 are the same or different and are unsubstituted or substituted alkyl groups, unsubstituted or substituted aryl groups, or unsubstituted or substituted cycloalkyl groups, more preferably, they are unsubstituted or substituted phenyl groups and if they are substituted, the substituents may be joined to form a closed structure. If the phenyls are substituted, the substituents preferably occupy 2 and 6 positions.

Preferably, R3 and R4 are the same or different, hydrogen, unsubstituted or substituted alkyl groups, unsubstituted or substituted aryl groups, or unsubstituted or substituted cycloalkyl groups, more preferably, they are unsubstituted or substituted alkyl groups. Optionally R3 and R4 may also be linked together to form a cyclohexyl ring.

In another embodiment according to the present invention, R1 with R3 or R2 with R4 are linked together to form a ring.

Preferably, R5 is hydrogen, unsubstituted or substituted alkyl groups, unsubstituted or substituted aryl groups, more preferably hydrogen or methyl.

Preferably, Z is selected from N, P, O or S.

Preferably, R6, R7, R8, R9 and R10 are the same or different, hydrogen, unsubstituted or substituted alkyl groups, unsubstituted or substituted aryl groups, or unsubstituted or substituted cycloalkyl groups. R8, R9 and R10 can be linked together to form a ring, for example a pyridine, a quinoline, an isoquinoline, a pyrrolyl, a furyl or a thiophenyl group.

Examples of formula III include 2-(bromomethyl)-5-nitrofuran, 2-(bromomethyl)-1,3-dioxalane, 2-(bromomethyl)tetrahydro-2H-pyran, 2-(bromomethyl)-5-trifluoromethyl) furan, 3(-bromomethyl)pyridazine, 2-bromomethylpyridine, 1-bromo-2-ethoxyethane, 2-bromoethylacetate, 1-bromo-2-(2-methoxyethoxy)ethane, [(2-bromoethoxy)methyl]benzene and 3-(bromomethyl)-2,4,10-trioxaadamantane, 2-bromo-N,N-dimethylaniline.

The invention also discloses a catalyst component of formula IV:

IV resulting from the complexation of ligand I with the metallic salt $MX'_n$ in a solvent, wherein M is a metal Group 3 to 10 of the periodic Table, X' is the same or different and can be a halogen, alcoholate, or substituted or unsubstituted hydrocarbyl and n is the valence of M.

Preferably, M is Ti, Zr, Hf, V, Cr, Mn, Fe, Co, Ni, Pd or rare earths. More preferably, it is Cr or Fe.

The metal is complexed with the two nitrogen atoms of the starting beta-diimine and during the complexation reaction, the complex folds around the carbon atom joining atom Z to the metal to form a three dimensional scorpion-like structure.

The solvent may be selected from dichloromethane or tetrahydrofuran and the complexation reaction is carried out at room temperature.

The present invention also discloses an active catalyst system comprising the single site catalyst component of formula IV and an activating agent having an ionising action.

Suitable activating agents are well known in the art. The activating agent can be an aluminium alkyl represented by formula $AlR^+_n X_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively, it can be aluminoxane and comprise oligomeric linear and/or cyclic alkyl aluminoxanes represented by formula for oligomeric, linear aluminoxanes and by formula for oligomeric, cyclic aluminoxane, wherein n is 1-40, preferably 1-20, m is 3-40, preferably 3-20 and R* is a $C_1$-$C_8$ alkyl group and preferably methyl or isobutyl.

Preferably, the activating agent is methylaluminoxane (MAO) or tetra-isobutyldialuminoxane (IBAO), more preferably, it is IBAO.

The amount of activating agent is selected to give an Al/M ratio of from 100 to 3000, preferably of from 500 to 2000. The amount of activating agent depends upon its nature, the preferred Al/M ratio being of about 2000.

Suitable boron-containing activating agents may comprise a triphenylcarbenium boronate such as tetrakis-pentafluorophenyl-borato-triphenylcarbenium as described in EP-A-0427696, or those of the general formula $[L'-H]+[B\ Ar_1\ Ar_2\ X_3\ X_4]$— as described in EP-A-0277004 (page 6, line 30 to page 7, line 7).

The amount of boron-containing activating agent is selected to give a B/M ratio of from 0.5 to 5, preferably of about 1.

In another embodiment, according to the present invention, the single site catalyst component of formula IV may be deposited on a conventional support. Preferably, the conventional support is silica impregnated with MAO. It may also be an activating support such as a fluorided alumina silica.

The present invention further discloses a method for preparing an active catalyst system that comprises the steps of:

a) providing a beta-diimine ligand precursor of formula II;
b) reacting the beta-diimine ligand precursor of formula II with compound III;
c) retrieving the scorpion-like ligand I
d) complexing the ligand obtained in step c) with a metallic salt $MX'_n$;
e) retrieving a catalyst component of formula IV;
f) activating with an activating agent having an ionising action;
g) optionally adding a cocatalyst
h) retrieving an active oligomerisation or polymerisation catalyst system.

Alternatively, in step f) catalyst component IV is deposited on a support impregnated with an activating agent or on an activating support containing fluor.

The cocatalyst may be selected from triethylaluminium, triisobutylaluminum, tris-n-octylaluminium, tetraisobutyl-dialuminoxane or diethyl zinc.

The active catalyst system is used in the oligomerisation and in the polymerisation of ethylene and alpha-olefins.

The present invention discloses a method for the oligomerisation or the homo- or co-polymerisation of ethylene and alpha-olefins that comprises the steps of:

a) injecting the active catalyst system into the reactor;
b) injecting the monomer and optional comonomer either before or after or simultaneously with step a);
c) maintaining under polymerisation conditions;
d) retrieving the oligomers and/or polymer.

The pressure in the reactor can vary from 0.5 to 50 bars, preferably from 5 to 25 bars.

The polymerisation temperature can range from 10 to 100° C., preferably from 50 to 85° C.

The preferred monomer and optional comonomer can be selected from ethylene, propylene or 1-hexene. Alternatively, the optional comonomer can be a polar functionalised alpha-olefin.

With a catalyst activated by MAO, the polymer formed is characterized by a melting point comprised between 100 and 135° C., preferably between 125 and 131° C. as measured by Differential Scanning Calorimetry (DSC) method. It has a multimodal molecular weight distribution with a molecular weight Mw of from 50000 to 500000, preferably of from 75000 to 250000, and a molecular weight distribution of 15 to 50 depending on the solvent. The molecular weight distribution is measured by the polydispersity index D defined as the ratio Mw/Mn of the weight average molecular weight Mw over the number average molecular weight Mn. Molecular weights are measured by Gel Permeation Chromatography (GPC).

With a catalyst activated by IBAO, the polymer formed is characterised by a melting point of about 135° C. as measured by Differential Scanning Calorimetry (DSC) method. It has a broad monomodal molecular weight distribution with a molecular weight Mw of 765000, and a molecular weight distribution of 25. The molecular weight distribution is measured by the polydispersity index D defined as the ratio Mw/Mn of the weight average molecular weight Mw over the number average molecular weight Mn. Molecular weights are measured by Gel Permeation Chromatography (GPC). $^{13}C$ NMR analysis showed the presence of linear (12 per 10000 carbon atoms) and isobutyle (10 per 10000 C atoms) saturated end chains. No short chain branching were detected.

With a supported catalyst, the polymer formed has a monomodal molecular weight distribution with a molecular weight Mw of from 150000 to 350000, preferably of from 180000 to 280000, and a molecular weight distribution of 5 to 20. It has a melting point comprised between 125 and 135° C. It has no short chain branching detectable by $^{13}C$ NMR analysis but it has long chain branching. The presence of the long chain branching is indicated by RDA analysis.

Throughout this description, LCB means chains long enough for entanglements to occur.

In order to quantify LCB concentration with rheology, we have adapted Shroff and Mpyridis definition of LCBI (Long Chain Branching Index) to our high molecular weight PE samples. (R. N. Shroff and H. Mpyridis, Macromolecules, 32, 8454, 1999.) As explained by those authors, LCBI quantifies the rheological effect of LCB (enhancement of shear viscosity at low shear rates) for narrow and broad molecular weight distribution (MWD) samples with sparse amount of LCB, that is LCB concentration typically too low to be detected by 13C NMR (for homopolymers PE) or by solution techniques such as size exclusion chromatography (SEC) coupled with on-line viscosity or light scattering detectors. DRI (Dow Rheology Index) which is another LCB indicator described in lai et al. (S. Lai, T. A. Plumley, T. I. Butler, G. W. Knight, C. I. Kao, SPE Antec Techn. Papers, 40, 1814, 1994) is not suitable to quantify LCB in polyethylene resins with polydispersity index larger than 4. DRI is thus not suitable to gauge LCB in our PE resins with broad MWD.

According to those authors, LCBI is defined as the ratio of intrinsic viscosities of PE resins estimated by rheology to that determined via solution techniques.

$$LCBI = \frac{[\eta]_{rheo}}{[\eta]_{sol}} - 1$$

wherein $[\eta]_{rheo}$ and $[\eta]_{sol}$ are the intrinsic viscosities obtained respectively from rheology or via solution.

Thus, LCBI is zero for linear samples and is above zero for polyethylene containing long chain branching. A high level of LCB is encountered with LCBI above 0.8. Instead of determining intrinsic viscosity from the relative viscosity at 0.2 dg/min as explained in their publication, we calculate intrinsic viscosity value via solution (expressed in dl/g) in terms of weight average molecular weight Mw (expressed in Da) obtained by size exclusion chromatography (SEC) with equation $$[\eta]_{sol} = 5.25 * 10^{-4} (M_w)^{0.76}$$

Zero shear viscosity ($\eta_0$) (expressed in Pa·s) is also related to $M_w$ (expressed in Da) by equation $$\eta_0 = 3.834 * 10^{-16} (M_w)^{3.855}$$

Zero shear viscosity is estimated by fitting with Carreau-Yasuda flow curve at 190° C., obtained by oscillatory shear rheology on ARES equipment in the linear viscoelasticity domain. Circular frequency (W in rad/s) varies from 0.05-0.1 rad/s to 250-500 rad/s and the shear strain is typically 10%.

The intrinsic viscosity inferred from rheology can thus be expressed as $$\eta = \eta_0 / (1 + (W^* \tau)^b)^{((1-n)/b)}$$

wherein $\tau$, b and n are fitting parameters called relaxation time, breadth parameter and power-law parameter, respectively.

The LCBI is thus rewritten as $$LCBI = \frac{0.5747 * (\eta_0)^{0.19714}}{5.25 * 10^{-4} (M_w)^{0.76}} - 1$$

In order to increase the accuracy in estimating zero shear viscosity, a frequency sweep experiment having a typical range of 0.1-250 rad/s, is combined with a creep experiment, in order to extend the frequency range to values down to $10^{-4}$ $s^{-1}$ or lower, and taking the usual assumption of equivalence of angular frequency (rad/s) and shear rate.

Frequency sweep experiments are performed using small parallel plates having a diameter of 8 mm that allow flow curve determination with as little as 0.1 g PE. Also, most tests are conducted at a temperature of 230° C. for polymers that do not exhibit homogeneous flow below that temperature.

Thus, LCBI is derived at a temperature of 230° C. using extrapolated shear viscosity at 0.001 $s^{-1}$ as follows.

$$LCBI_{230} = \frac{0.58 * (\eta_{0.001})^{0.2096}}{5.25 * 10^{-4} (M_w)^{0.76}} - 1$$

The subscript 230 recalls that LCBI is determined from frequency sweep experiments conducted at 230° C.

The relationship between viscosity and Mw is established as usual with a series of linear polyethylene. The viscosity/Mw relationship was established with a series of 15 linear PE having a polydispersity index between 2 and 18.

ZN or metallocene-produced polyethylene known to be linear have a LCBI of 0+/−0.1. Thus, PE with LCB are detected above LCBI of 0.1-0.2

EXAMPLES

Preparation of Catalyst Component

Synthesis of the Ligand 1.

Step 1.

The beta-diimine was synthesised according to the published procedure of Feldman and al. (*Organometallics* 1997, 16, p. 1514).

Step 2.

760 mg (3 mmol) of 2-bromomethylpyridine•HBr and 436 mg (3.15 mmol) of potassium carbonate were degassed under vacuum for 1 hour. 10 mL of dry acetone were added and the mixture was stirred under argon for 6 hours at room temperature (about 25° C.). The solvent was removed and the 2-bromomethylpyridine was extracted with 3×10 mL of diethyl ether under inert atmosphere. The solvent was removed to afford a pink oil with quantitative yield.

Step 3.

1.26 g (3 mmol) of beta-diimine were dissolved in 15 mL of dry THF under argon. The solution was cooled to a temperature of −20° C. and 2 mL (3.15 mmol) of n-BuLi (1.6 M in hexane) were added dropwise. The colourless solution turned immediately to bright yellow and was stirred at room temperature for 30 minutes. The solution was cooled to a temperature of −20° C. and a solution of 2-bromomethylpyridine in 10 mL of dry THF was added by canula. The solution was allowed to warm to room temperature and was stirred overnight, before being heated at 80° C. for 6 hours under reflux. After that time, the solvent was evaporated to dryness. The residue was taken with 10 mL of dichloromethane and filtered over neutral alumina. The solution was evaporated to afford a yellow oil purified by column chromatography (SiO$_2$, pentane:diethyl ether 95:5 to 80:20). 910 mg of the expected product were obtained as pale yellow oil containing isomers 1a and 1b, with a yield of 60%.

1a

1b

The isomers were characterised as follows:
C$_{35}$H$_{47}$N$_3$
M=509.77 g.mol$^{-1}$
$^1$H NMR (500 MHz, CDCl$_3$) results:

Isomer 1a: δ=1.10 (m, 12H, CH$_3$ iPr), 1.21 (dd, 12H, J=6.8 Hz, CH$_3$ iPr), 1.92 (s, 6H, CH$_3$CN), 2.53 (sept, 2H, J=6.8 Hz, CH iPr), 2.60 (sept, 2H, J=6.8 Hz, CH iPr), 3.65 (d, 2H, J=7.5 Hz, CH$_2$), 4.70 (t, 1H, J=7.5 Hz, CH), 7.11 (m, 2H, CH para Ph), 7.17 (br s, 4H, CH meta Ph), 7.22 (m, 1H, H5 pyr), 7.38 (d, 1H, J=7.5 Hz, H3 pyr), 7.66 (td, 1H, J=7.5 Hz, J=1.8 Hz, H4 pyr), 8.66 (d, 1H, J=5 Hz, H6 pyr).

Isomer 1b: δ=1.07 (m, 12H, CH$_3$ iPr), 1.13 (d, 12H, J=6.9 Hz, CH$_3$ iPr), 1.78 (s, 6H, CH$_3$CN), 3.20 (sept, 4H, J=6.9 Hz, CH iPr), 4.06 (s, 2H, CH$_2$), 7.09 (m, 2H, CH para Ph), 7.13 (m, 4H, CH meta Ph), 7.18 (m, 1H, H5 pyr), 7.33 (d, 1H, J=7.8 Hz, H3 pyr), 7.68 (m, 1H, H4 pyr), 8.61 (d, 1H, J=5 Hz, H6 pyr).

Preparation of Fe(II) Complex 2.

210 mg (0.4 mmol) of beta-diimine-methylpyridine (1a and 1b) and 84 mg (0.4 mmol) of iron (II) chloride tetrahydrate were degassed under vacuum for 1 hour. 10 mL of dry tetrahydrofuran (THF) were added and the mixture was stirred under argon overnight at room temperature. The solid was filtered off and the filtrate was concentrated to dryness to afford 228 mg of Fe(II) complex 2 as a brown-yellow powder with a yield of 87%. It had formula C$_{35}$H$_{47}$Cl$_2$FeN$_3$ and a molar weight of 636.51 g.mol$^{-1}$.

2

Mass spectroscopy: ESI (Electron Spray Ionisation), solvent=CH$_3$CN: m/z=601.28 [M-Cl]$^+$. The calculations for C$_{35}$H$_{47}$FeClN$_3$ gave a value of 600.2808.

Preparation of Cr(III) Complex 3.

210 mg (0.4 mmol) of beta-diimine-methylpyridine and 162 mg (0.4 mmol) of chromium (III) chloride tetrahydrofuran were degassed under vacuum for 1 hour. 10 mL of dry tetrahydrofuran were added and the mixture was stirred under argon overnight at room temperature. The solid was filtered off and the filtrate concentrated to dryness to afford 274 mg of Cr(III) complex 3 as a pink powder with a yield of 95%. It had formula C$_{35}$H$_{47}$Cl$_3$CrN$_3$ and a molar weight of 668.13 g.mol$^{-1}$.

3

Mass spectroscopy: ESI (Electron Spray Ionisation), solvent =CH$_3$CN: m/z=631.25 [M-Cl]+. The calculations for C$_{35}$H$_{47}$CrCl$_2$N$_3$ gave a value of 631.2552.

Preparation of Co(II) Complex 4.

51 mg (0.1 mmol) of beta-diimine-methylpyridine (1a and 1b) and 13 mg (0.1 mmol) of cobalt (II) chloride were degassed under vacuum for 1 hour. 5 mL of dry dichloromethane were added and the mixture was stirred under argon overnight at room temperature. The solid was filtered off and the filtrate was concentrated under vacuum to approximately 2 mL. 20 mL of dry pentane were added to precipitate the complex. The solvent was removed by filtration under argon and the resulting powder washed twice with 5 mL of dry pentane. The solid was dried under vacuum to afford 44 mg of Co(II) complex 4 as a green powder with a yield of 69%. It had formula $C_{35}H_{47}Cl_2CoN_3$ and a molar weight of 639.61 g.mol$^{-1}$.

Preparation of Fe(III) Complex 5.

51 mg (0.1 mmol) of beta-diimine-methylpyridine (1a and 1b) and 13 mg (0.1 mmol) of iron (III) chloride were degassed under vacuum for 1 hour. 5 mL of dry tetrahydrofuran (THF) were added and the mixture was stirred under argon overnight at room temperature. The solid was filtered off and the filtrate was concentrated to dryness to afford 45 mg of Fe complex 5 as a brown-yellow powder with a yield of 67%. It had formula $C_{35}H_{47}Cl_3FeN_3$ and a molar weight of 671.97 g.mol$^{-1}$.

Synthesis of Ligands 6

Using the procedure described for ligand 1 (step 1, 2 and 3), ligand 6 was obtained with a yield of 61%.

$^1$H NMR (500 MHz, CDCl$_3$): δ=1.26 (s, 18H, CH$_3$ tBu), 2.00 (s, 6H, CH$_3$CN), 3.63 (d, 2H, J=7.5 Hz, CH$_2$), 4.44 (t, 1H, J=7.5 Hz, CH), 6.25 (d, 2H, J=7.5 Hz), 7.05 (m, 6H), 7.34 (t, 2H, J=7.5 Hz), 7.62 (t, 1H, J=7.5 Hz), 8.59 (d, 1H, J=5H).

Synthesis of Ligands 7

Using the procedure described for ligand 1 (step 1, 2 and 3), ligand 7 was obtained with a yield of 41%.

$^1$H NMR (500 MHz, CDCl$_3$): δ=1.80 (s, 6H, CH$_3$), δ=1.84 (s, 12H, CH$_3$), 2.25 (s, 6H, CH$_3$), 3.60 (d, 2H, J=7.5 Hz, CH$_2$), 4.53 (t, 1H, J=7.5 Hz, CH), 6.90 (s, 4H), 7.1-7.25 (m, 1H), 7.30-7.80 (m, 3H), 8.58 (m, 1H).

Preparation of Complexes 8

Using the procedure described for complex 3, complex 8 was obtained with a yield of 68%.

Preparation of Complexes 9

Using the procedure described for complex 3, complex 9 was obtained with a yield of 63%.

9

12

Preparation of Complex 10.

150 mg (0.3 mmol) of ligand 1 and 36 mg (0.3 mmol) of chromium (II) chloride were degassed under vacuum for 1 hour. 10 mL of dry tetrahydrofuran were added and the mixture was stirred under argon overnight at room temperature. The reaction mixture was concentrated to 2 ml and 10 mL of pentane was added. The solid was filtered off and washed twice with 5 mL of pentane. The solid was dried to afford 186 mg of Cr(II) complex 10 as a green powder with a yield of 58%.

10

Preparation of the Complexes 11

Using the procedure described for complex 10, complex 11 was obtained with a yield of 37%.

11

Preparation of the Complexes 12

Using the procedure describe for complex 10, complex 12 was obtained with a yield of 46%.

High Pressure Polymerisation of Ethylene.

Ethylene polymerisation reactions were performed in a 20 mL stainless steel autoclave containing a glass insert, fitted with mechanical stirring, external thermocouple and pressure gauge and controlled by computer. In a typical reaction run, 4 mL of dry solvent (toluene or n-heptane) were introduced into the reactor, the temperature was raised to 50° C. and the ethylene pressure was raised to 15 bar and continuously fed. In a argon-filled glove box, about 5 μmol of the appropriate catalyst were weighted, activated with an amount of methylaluminoxane (MAO 30% wt in toluene) or tetraisobutyldialuminoxane (IBAO 10 wt % in toluene) activator in an amount appropriate to obtain a ratio [Al]:[M] of 2000 and diluted with toluene to a final volume of 2 mL. 200 μL of the solution of the activated catalyst were placed inside the reactor. The injection loop was rinsed with 800 μL of solvent. After 1 hour or a consumption of 12 mmol of ethylene, the reaction was quenched with isopropanol and an aliquot analysed by gas chromatography. The gas chromatographic analysis of the reaction products were performed on a Trace GC apparatus with a Petrocol capillary column (methyl silicone, 100 m long, i.d. 0.25 mm and film thickness of 0.5 μm) working at a temperature of 35° C. for 15 min and then heated to a temperature of 250° C. at a heating rate of 5° C./min. The remaining reaction mixture was quenched with MeOH/HCl and the polymer was filtered, washed with methanol and dried at a temperature of 50° C., under vacuum, for a period of time of 24 hours.

The reaction conditions for each example are displayed in Table I and the results are displayed in Table II and in Table III.

TABLE I

| Example | Catalyst | Amt catalyst nmol | Solvent | Activator | Time min |
|---|---|---|---|---|---|
| 1 | 2 | 500 | toluene | MAO | 60 |
| 2 | 2 | 500 | n-heptane | MAO | 60 |
| 3 | 3 | 500 | toluene | MAO | 30 |
| 4 | 3 | 500 | n-heptane | MAO | 60 |
| 5 | 3 | 500 | n-heptane | MAO | 60 |
| 6 | 3 | 494 | n-heptane | IBAO | 60 |
| 7 | 8 | 507 | n-heptane | MAO | 60 |
| 8 | 9 | 462 | n-heptane | MAO | 60 |
| 9 | 10 | 506 | n-heptane | MAO | 60 |
| 10 | 8 | 507 | n-heptane | IBAO | 60 |
| 11 | 9 | 462 | n-heptane | IBAO | 60 |
| 12 | 10 | 506 | n-heptane | IBAO | 60 |

TABLE II

| Ex. | PE mg | C2 cons. mmol | Act.[a] | % C4 Total | % αC4 | % C6 Total | % αC6 | % > C6 | % αC2n lin. |
|---|---|---|---|---|---|---|---|---|---|
| 1 | 4 | 0.37 | 20 | Traces | — | — | — | — | — |
| 2 | 0 | 0.46 | 25 | Traces | — | — | — | — | — |
| 3 | 16 | 12.03 | 1350 | 16 | 99.8 | 27 | 97 | 57 | 95 |
| 4 | 62 | 2.55 | 140 | 8.5 | 99.5 | 16.5 | 88 | 75 | 76 |
| 5 | 43 | 2.85 | 160 | 7.5 | 100 | 16.5 | 89 | 76 | 86 |
| 6 | 551 | 9.96 | 1120[b] | — | — | — | — | — | — |
| 7 | 68 | 2.44 | 135 | Traces | — | — | — | — | — |
| 8 | 57 | 2.99 | 181 | Traces | — | — | — | — | — |
| 9 | 60 | 1.62 | 119[b] | Traces | — | — | — | — | — |
| 10 | 634 | 9.92 | 1252[b] | — | — | — | — | — | — |
| 11 | 541 | 9.48 | 1170[b] | — | — | — | — | — | — |
| 12 | 489 | 757 | 967[b] | — | — | — | — | — | — |

[a] the activity is measured in kg of ethylene consumed per mol of metal M per hour.
[b] the activity is measured in kg of polyethylene per mol of metal M per hour.

TABLE III

| | | DSC | | | GPC | | |
|---|---|---|---|---|---|---|---|
| Example | PE mg | Tm (° C.) | ΔH J·g$^{-1}$ | LCBI | Mw | Mn | MWD |
| 4 | 62 | 128.5 | 163.9 | / | / | / | / |
| 5 | 43 | 127.7 | 170.3 | | 78270 | 1620 | 48.2 |
| 6 | 551 | 133.8 | 168.4 | | 765300 | 31300 | 24.5 |

Figure 1:
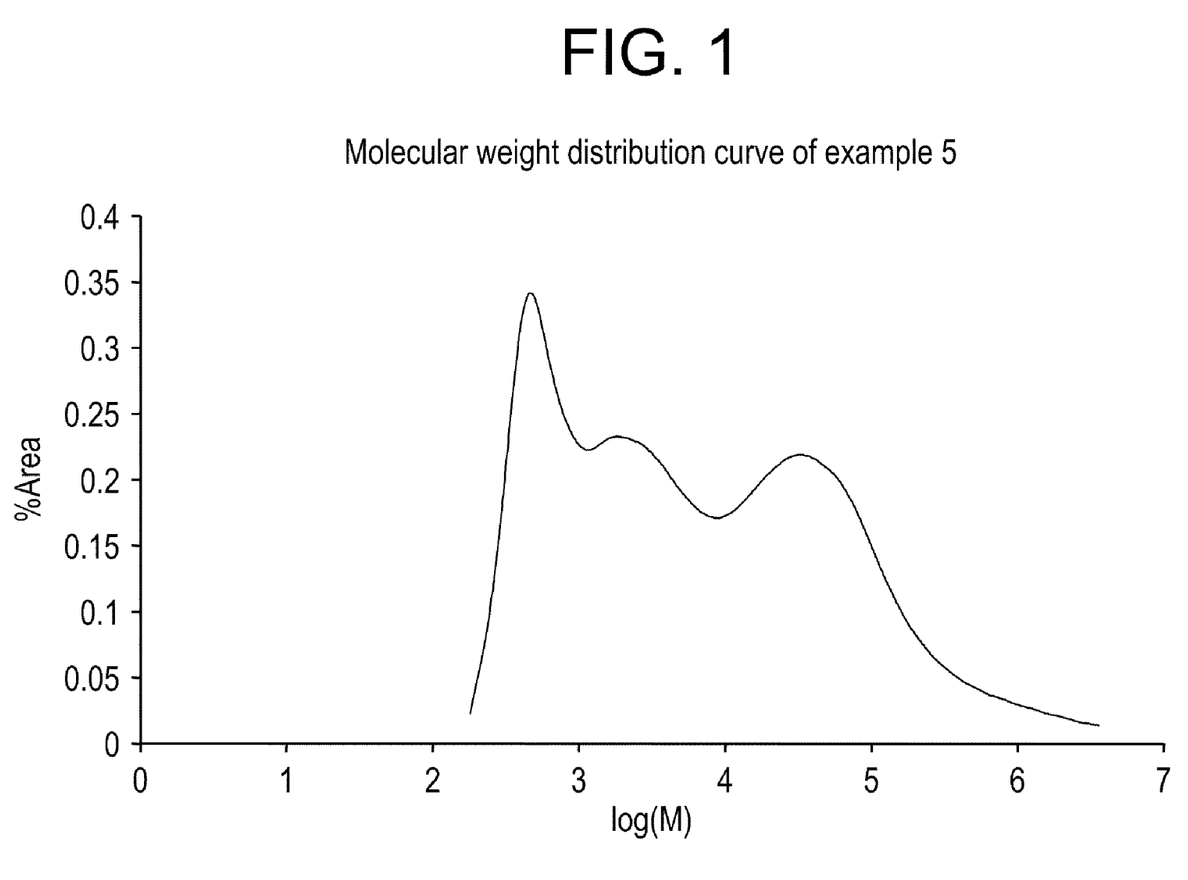
FIG. 1 represents the molecular weight distribution of the polyethylene obtained in example 5.

The molecular weight distribution for example 5 is represented in FIG. 1.

Oligomerisation of 1-Hexene.

In a argon-filled glove box, about 7.5 μmol of the appropriate catalyst were weighted, activated with an amount of methylaluminoxane (MAO) activator, 30% wt in toluene, suitable to give a [Al]:[M] ratio of 2000 and diluted with toluene to a final volume of 4.5 mL. 3 mL of the solution of the activated catalyst were placed in a Schlenk tube containing 5 mL of 1-hexene. The solution was stirred at a temperature of 30° C. for 1 hour. The mixture was quenched with slightly acidified methanol. The layers were separated. The toluene layer was concentrated to dryness to afford oligomers. The gas chromatographic analysis of the reaction products was done on a Trace GC apparatus with a Petrocol capillary column (methyl silicone, 100 m long, i.d. 0.25 mm and film thickness of 0.5 μm) working at a temperature of 100° C. for 4 min and then heated to a temperature of 250° C. at a heating rate of 8° C./min.

The results are displayed in Table IV.

TABLE IV

| Cata. | Amt cata. μmol | Time min | Yield mg | Activity* | % C12 | % C18 | % C24 |
|---|---|---|---|---|---|---|---|
| 2 | 5 | 60 | 34 | 4.5 | 0 | 0 | 0 |
| 3 | 5 | 60 | 277 | 55 | 57 | 35 | 8 |

*activity expressed in kg of oligomer per mol of metal per hour.

Polymerisation of Ethylene with Supported Catalysts

Ethylene polymerisation reactions were carried out in a 130 ml stainless steel autoclave equipped with mechanical stirring and a stainless steel injection cylinder. In a typical reaction run, the reactor was first dried under nitrogen flow at 100° C. during 10 min. Then it was cooled down to the reaction temperature (50° or 85° C.) and 35 ml of isobutane were introduced into the reactor with a syringe pump, followed by the comonomer if required. The pressure was adjusted to the desired value (14.8 or 23.8 bar) with ethylene. In an argon-filled glove box, 300 mg of the supported catalyst (complex 3 deposited on MAO impregnated silica, at 2 wt % based on the total weight of the supported catalyst), the cocatalyst and 0.6 ml of n-hexane were placed into the injection cylinder. The valve was closed and the cylinder was connected to the reactor under nitrogen flow. The active catalyst mixture was then introduced into the reactor with 40 ml of isobutane. After 30 minutes or 1 hour, the reactor was cooled down to room temperature and slowly depressurised, and the polymer was recovered. The polymerisation results are displayed in Table V.

TABLE V

Polymerisation results with supported Cr(III) Complex

| Example | Cr complex | T (° C.)/ P (bar) | Cocatalyst | Time min. | PE g | Activity* g/g/h |
|---|---|---|---|---|---|---|
| 13 | 3 | 85/23.8 | TiBAl 25.6 mg | 60 | 1.5 | 4.8 |
| 14 | 3 | 85/23.8 | TiBAl 25.6 mg | 30 | 1.1 | 7.3 |
| 15 | 3 | 85/23.8 | IBAO 38.8 mg | 60 | 1.6 | 5.4 |
| 16 | 3 | 50/14.8 | TEAl 16.6 mg | 30 | 0.9 | 5.7 |
| 17[a] | 3 | 85/23.8 | TiBAl 25.6 mg | 60 | 0.7 | 2.4 |
| 18[b] | 3 | 85/23.8 | IBAO 38.8 mg | 60 | 0.7 | 3.5 |

Figure 2:
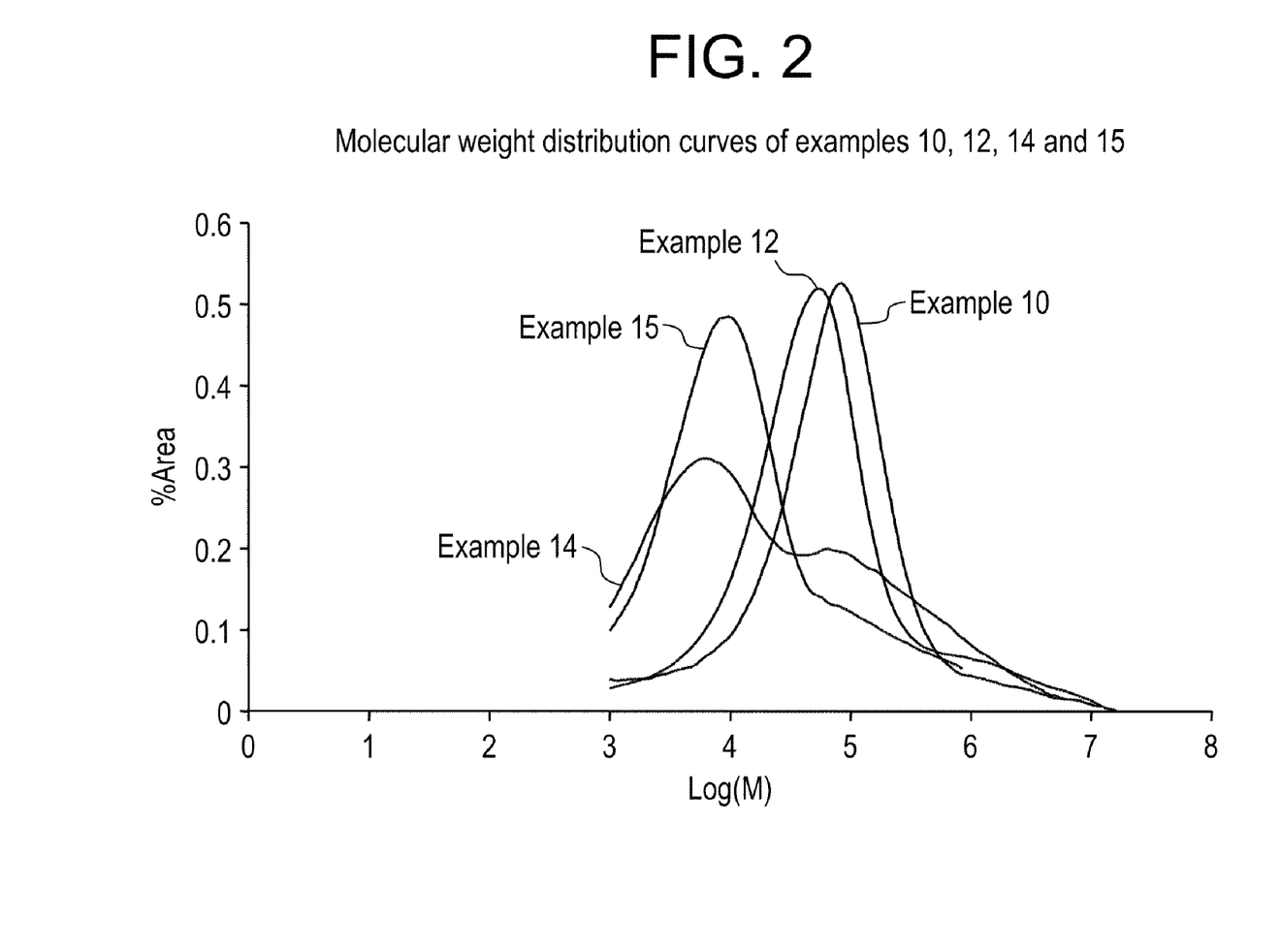
FIG. 2 represents the molecular weight distribution of the polyethylenes obtained in examples 9 and 11.

*Activity is expressed as g polyethylene per g catalyst per hour
[a] 0.01 Nl of H$_2$ was added
[b] 200 mg of catalyst was used and 1.6 ml of hexene was added The obtained polymers were characterized by GPC in TCB at 140° C., by DSC, by RDA at 230° C. and by $^{13}$C NMR in TCB at 135° C. The results are displayed in table VI and FIG. 2.

TABLE VI

Characterisation of the polyethylenes obtained with supported Cr(III) complex.

| | RDA | HT-GPC | | | $^{13}$C NMR | DSC |
|---|---|---|---|---|---|---|
| Example | LCBI 230° C. | Mw (Da) | Mn (Da) | D | SCB (mol %) | Tm (° C.) |
| 13 | 1.38 | 197081 | 23430 | 8.4 | 0.12 | 130.3 |
| 15 | 01.29 | 265464 | 19365 | 13.7 | <0.1 | 131.7 |
| 17 | / | 193122 | 7178 | 26.9* | / | 128.8 |
| 18 | 2.47 | 243000 | 16200 | 15 | / | / |

*Bimodal

The $^{13}$C NMR analysis for examples 10 and 12, showed the absence of short chain branching (less than 0.1 mol %) and the presence of saturated and vinylic ends.

It can thus be seen that the polymers according to the present invention have a very high level of long chain branching, in fact much larger than the polymers prepared with bis-tetrahydroindenyl metallocene catalyst components known to have a high level of high chain branching and who exhibit a LCBI typically of from 0.5 to 1.

The invention claimed is:
1. A tridentate catalyst component of formula IV wherein $R_1$, $R_2$, $R_3$, $R_4$, $R_5$, $R_6$, $R_7$, $R_8$, $R_9$ and $R_{10}$ are each independently selected from hydrogen or unsubstituted or substituted hydrocarbyl and two or more groups can be linked together to form further ring or rings, with the restriction that $R_1$ and $R_3$, $R_2$ and $R_4$, and $R_9$ and $R_{10}$, cannot be simultaneously oxazoline, and
wherein Z is selected from groups 15 or 16 of the Periodic Table and m is the valence of Z minus one,
wherein M is Ti, Zr, Hf, V, Cr, Mn, Fe, Co, Ni, or Pd,
wherein X' are the same or different and are halogen or substituted or unsubstituted hydrocarbyl; and
wherein n is the valence of M and
characterised in that the complex folds around the carbon atom preceding Z to allow joining Z to metal M in order to form a 3 dimensional scorpion like structure.

2. The tridentate catalyst component of claim 1 wherein $R_1$ and $R_2$ are unsubstituted or substituted alkyl groups, unsubstituted or substituted aryl groups, or unsubstituted or substituted cycloalkyl groups.

3. The tridentate catalyst component of claim 1 wherein $R_1$ and $R_2$ are unsubstituted or substituted phenyl groups.

4. The tridentate catalyst component of claim 1 wherein $R_3$ and $R_4$ are unsubstituted or substituted alkyl groups, unsubstituted or substituted aryl groups, or unsubstituted or substituted cycloalkyl groups.

5. The tridentate catalyst component of claim 1 wherein $R_3$ and $R_4$ are unsubstituted or substituted alkyl groups.

6. The tridentate catalyst component of claim 5 wherein $R_3$ and $R_4$ are linked together to form a cyclohexyl ring.

7. The tridentate catalyst component of claim 1 wherein $R_5$ is hydrogen or methyl.

8. The tridentate catalyst component of claim 1 wherein Z is N, P, O or S.

9. The tridentate catalyst component of claim 1 wherein $R_6$, $R_7$, $R_8$, $R_9$ and $R_{10}$ are unsubstituted or substituted alkyl groups, unsubstituted or substituted aryl groups, or unsubstituted or substituted cycloalkyl groups.

10. The tridentate catalyst component of claim 1 wherein M is Ti, Zr, Hf, V, Cr, Mn, Fe, Co, Ni, or Pd.

11. The tridentate catalyst component of claim 1 wherein M is Cr.

12. A method for preparing the tridentate catalyst component of claim 1 by complexing a ligand of formula I with a metallic salt $MX'_n$ in a solvent, wherein all R's and M are as defined in claim 1,
wherein X is halogen or substituted or unsubstituted hydrocarbyl and n is the valence of M.

13. An active catalyst system comprising the tridentate catalyst component of claim 1 and an activating agent having an ionising action and optionally a cocatalyst.

14. An active catalyst system comprising the tridentate catalyst component of claim 1, an activating support and optionally a cocatalyst.

15. A method for oligomerising or homo- or co-polymerising ethylene and alpha-olefins that comprises:
a) injecting the active catalyst system of claim 13 into the reactor;
b) injecting ethylene monomer and optional comonomer either before or after or simultaneously with step a);
c) maintaining polymerisation conditions; and
d) retrieving oligomers or a polymer.

16. The method of claim 15 wherein the monomer and optional comonomer are selected from ethylene, propylene or 1-hexene.

17. The method of claim 16 wherein the optional comonomer is a polar functionalised alpha-olefin.

* * * * *